US012318569B2

(12) United States Patent
Miltenyi et al.

(10) Patent No.: US 12,318,569 B2
(45) Date of Patent: *Jun. 3, 2025

(54) STERILE CONNECTOR

(71) Applicant: Miltenyi Biotec B.V. & Co. KG, Bergisch Gladbach (DE)

(72) Inventors: Stefan Miltenyi, Bergisch Gladbach (DE); Winfried Schimmelpfennig, Teterow (DE); Carlo Pannen, Bergisch Gladbach (DE)

(73) Assignee: Miltenyi Biotec B.V. &Co. KG, Bergisch Gladbach (DE)

( * ) Notice: Subject to any disclaimer, the term of this patent is extended or adjusted under 35 U.S.C. 154(b) by 54 days.

This patent is subject to a terminal disclaimer.

(21) Appl. No.: 18/122,753

(22) Filed: Mar. 17, 2023

(65) Prior Publication Data

US 2023/0241368 A1 Aug. 3, 2023

Related U.S. Application Data

(63) Continuation-in-part of application No. 16/123,068, filed on Sep. 6, 2018, now Pat. No. 11,633,584.

(30) Foreign Application Priority Data

Sep. 20, 2017 (EP) .................................... 17192004

(51) Int. Cl.
*A61M 39/18* (2006.01)
*A61M 39/10* (2006.01)
(Continued)

(52) U.S. Cl.
CPC ............ *A61M 39/18* (2013.01); *A61M 39/14* (2013.01); *B01L 3/563* (2013.01); *A61M 2039/1027* (2013.01); *F16L 2201/44* (2013.01)

(58) Field of Classification Search
CPC .. A61M 39/14; A61M 39/146; A61M 39/165; A61M 39/18; A61M 39/22; A61M 39/16; A61M 2039/1027; A61M 2039/1066; B01L 3/563; B01L 2300/044; B01L 2300/0803; F16L 37/26; F16L 37/1225; F16L 2201/44

(Continued)

(56) References Cited

U.S. PATENT DOCUMENTS 243,822 A * 7/1881 Westinghouse, Jr. ... F16L 37/26
                                                          285/70
3,232,578 A * 2/1966 Cousins ................. A61C 17/13
                                                          433/95

(Continued)

*Primary Examiner* — Kenneth Rinehart
*Assistant Examiner* — Jonathan J Waddy
(74) *Attorney, Agent, or Firm* — Jaquelin K Spong (57) ABSTRACT

The invention is directed to an connector comprising a first part and a second part, each provided with a contact surface and at least one non-contact surface facing away from the contact surface, at least one opening in the contact surface having an fluid connection to at least one opening of the non-contact surface, a releasable covering of the opening in the contact surface, and complementary means for mechanically coupling the parts at the contact surfaces to form the connector. The complementary means for mechanically coupling the parts are configured to mechanically interlock with each other.

11 Claims, 7 Drawing Sheets

(51) Int. Cl.
*A61M 39/14* (2006.01)
*B01L 3/00* (2006.01)

(58) Field of Classification Search
USPC .......................................................... 600/133
See application file for complete search history.

(56) References Cited

U.S. PATENT DOCUMENTS

| | | | | |
|---|---|---|---|---|
| 3,865,411 A * | 2/1975 | Rowe | .......................... | F16K 7/18 285/915 |
| 4,432,755 A * | 2/1984 | Pearson | ................ | A61J 1/2089 604/905 |
| 4,850,350 A * | 7/1989 | Jackson | ............... | A61M 1/7413 604/35 |
| 5,810,398 A * | 9/1998 | Matkovich | ............ | A61M 39/18 604/209 |
| 5,894,011 A * | 4/1999 | Prosl | ..................... | A61M 39/18 210/636 |
| 5,947,954 A * | 9/1999 | Bonaldo | ............... | A61M 39/26 604/905 |
| 6,655,655 B1 * | 12/2003 | Matkovich | .......... | A61M 39/1011 604/905 |
| 11,633,584 B2 * | 4/2023 | Miltenyi | ............... | A61M 39/14 285/148.1 |
| 2008/0265561 A1 * | 10/2008 | Buchanan | ............ | B29C 66/857 604/28 |
| 2009/0232586 A1 * | 9/2009 | Diodati | ................... | F16L 37/32 403/14 |
| 2010/0230961 A1 * | 9/2010 | Johnson | .............. | F16L 37/0985 285/352 |
| 2013/0184688 A1 * | 7/2013 | Gagliardoni | ....... | A61M 39/1011 29/428 |
| 2013/0289517 A1 * | 10/2013 | Williams | ............... | F16L 37/098 604/500 |
| 2015/0028586 A1 * | 1/2015 | Gerst | ................. | A61M 39/1011 285/352 |
| 2015/0345689 A1 * | 12/2015 | Selker | .................... | B65B 55/16 422/534 |
| 2016/0053927 A1 * | 2/2016 | Whitaker | ............... | F16L 29/007 137/15.09 |
| 2016/0305574 A1 * | 10/2016 | Burdge | ................. | A61M 39/26 |
| 2017/0080201 A1 * | 3/2017 | Lee | ..................... | A61M 39/105 |
| 2017/0284584 A1 * | 10/2017 | Kesselaar | ......... | A61M 39/1011 |

* cited by examiner

STERILE CONNECTOR

CROSS REFERENCE TO RELATED APPLICATIONS

This nonprovisional US Patent Application is a Continuation-In-Part, claiming priority to U.S. nonprovisional application Ser. No. 16/123,068, filed Sep. 6, 2018. This prior application is incorporated by reference in its entirety for all purposes.

STATEMENT REGARDING FEDERALLY SPONSORED RESEARCH

Not applicable.

STATEMENT REGARDING MICROFICHE APPENDIX

Not applicable.

BACKGROUND

The present invention is directed to a connector for sterile connection of tubing sets.

In some technical fields like medicine or biology, it is often required to transfer fluids from one container or device to another under sterile conditions, i.e. at best in absence of any contamination by pollutants, dust, bacteria, viruses, or spores or the like. Unavoidable, connections between the containers have to be provided which may jeopardize sterility.

Devices for sterile connection of tubes, containers or bags in an unsterile environment are known in many variants as "sterile connectors" or simply "connectors". Sterile connectors are known in various modifications, but the most safe connectors in view of sterility usually comprise at least two parts, each connected to a container, which are then mechanically interlocked to provide a fluid connection between the containers. Particular useful to maintain sterility of the devices are connector parts, each provided with an adhesive film protecting the sterile side of the device, which are then removed simultaneously to give way for the fluids.

Examples for such connectors are disclosed in U.S. Pat. Nos. 9,295,825 and 3,865,411. Both publications describe sterile connectors wherein two parts are mechanically combined and a releasable film is removed from both parts at once, the connection is made. By simultaneously removing the releasable films, a sterile passage between the parts i.e. through the connector is provided.

Maintaining sterility is especially difficult in connecting freezing bags, which are commonly used for long-term storage of sterile samples at deep temperatures as for example provided by liquid nitrogen. Besides that all materials used for deep temperature storage need to be certified for stability, the connector still needs to provide a water- and gas tight connection in presence of condensing moisture, ice and unsterile air. A further cause of sterility loss is mishandling the connector, for example by incomplete mechanical connection of the connector parts, premature removing one or both releasable films or not simultaneous removing the releasable films.

Object of the invention was to provide a connector with build-in features to maintain sterility and to avoid mishandling and/or unintentionally abolishing sterility, especially under deep temperature storage conditions.

One ongoing issue with available biocompatible connectors is the possibility of contamination of the environment or user from the biological materials or reagents.

SUMMARY

Accordingly, the invention is directed to a Connector comprising a first part and a second part, each provided with a contact surface and at least one non-contact surface facing away from the contact surface
- at least one opening in the contact surface having an fluid connection to at least one opening of the non-contact surface
- a releasable covering of the opening in the contact surface
- complementary means for mechanically coupling the parts at the contact surfaces to form the connector
- characterized in that the complementary means for mechanically coupling the parts are configured to mechanically interlock with each other by counter-rotating of the first and second part; and
- the openings in the contact surfaces are configured to be brought to match at least in part to provide fluid communication through the openings by counter-rotating of the first and second part.

Furthermore, the invention is directed to a tubing set comprising at least one tube, at least one freeze bag and at least one connector of the invention. The freeze bag of such tubing set may comprise at least one recess to accommodate least one connector. This variant greatly simplifies the storage of the freeze bag in a low-temperature environment without struggling with the tubing.

The connector according to the invention is configured to allow fluid communication only when sterility of the fluids is ensured. To this end, the connector is provided with mechanical safety features and releasable coverings of the opening. Further, the connector can be stored with the freezing bag in a flat manner since the openings of the connector for attaching the tubing set are optionally positioned orthogonal to each other.

BRIEF DESCRIPTION OF THE DRAWINGS

In the figures discussed below, similar reference numbers are intended to refer to similar structures, and the structures are illustrated at various levels of detail to give a clear view of the important features of this novel device. It should be understood that these drawings do not necessarily depict the structures to scale, and that directional designations such as "top," "bottom," "upper," "lower," "left" and "right" are arbitrary, as the device may be constructed and operated in any particular orientation.

FIG. 7 shows another embodiment of the sterile connector, using an adhesive foil.

It should be understood that the drawings are not necessarily to scale, and that like numbers may be may refer to like features.

DETAILED DESCRIPTION

The present invention is directed to a connector for tubing sets, especially for freezing bags which enables a safe and sterile connection of at least two tubes in an unsterile environment. A preferred application of the connector is to connect a sterile sample in a freezing bag to a sterile tubing set in an unsterile environment.

The connector comprises a first and a second part, each provided with complementary means for mechanically coupling of the parts at the contact surfaces by counter-rotating of the parts. The term "counter-rotating of the parts" shall mean that the parts are brought in contact with the respective contact surfaces and then are rotated in opposite directions around a common rotational axis and includes the rotation of one part against the other part in an idle (non-rotational) state. For this propose, the connector is provided with complementary means for mechanically coupling 11, 21, which interact by counterrotation of the parts like a bayonet coupling. Further, appropriate means for mechanically interlocking the parts in the final position may be provided, for example flap (13a) shown in FIG. 3 locks into opening or recess 23a in counterpart 23.

The first and second part of the connector are optionally provided with means to optically indicate the relative position of the first and second part to each other during counter-rotating of the parts. Such means can be markings on the parts, for example printed signs or any three-dimensional object/form extending from the parts which can be "felt" when counterrotating the parts during the closing process. For example, objects 13 and 23 shown in the figures may serve as such markings.

Figure 1:
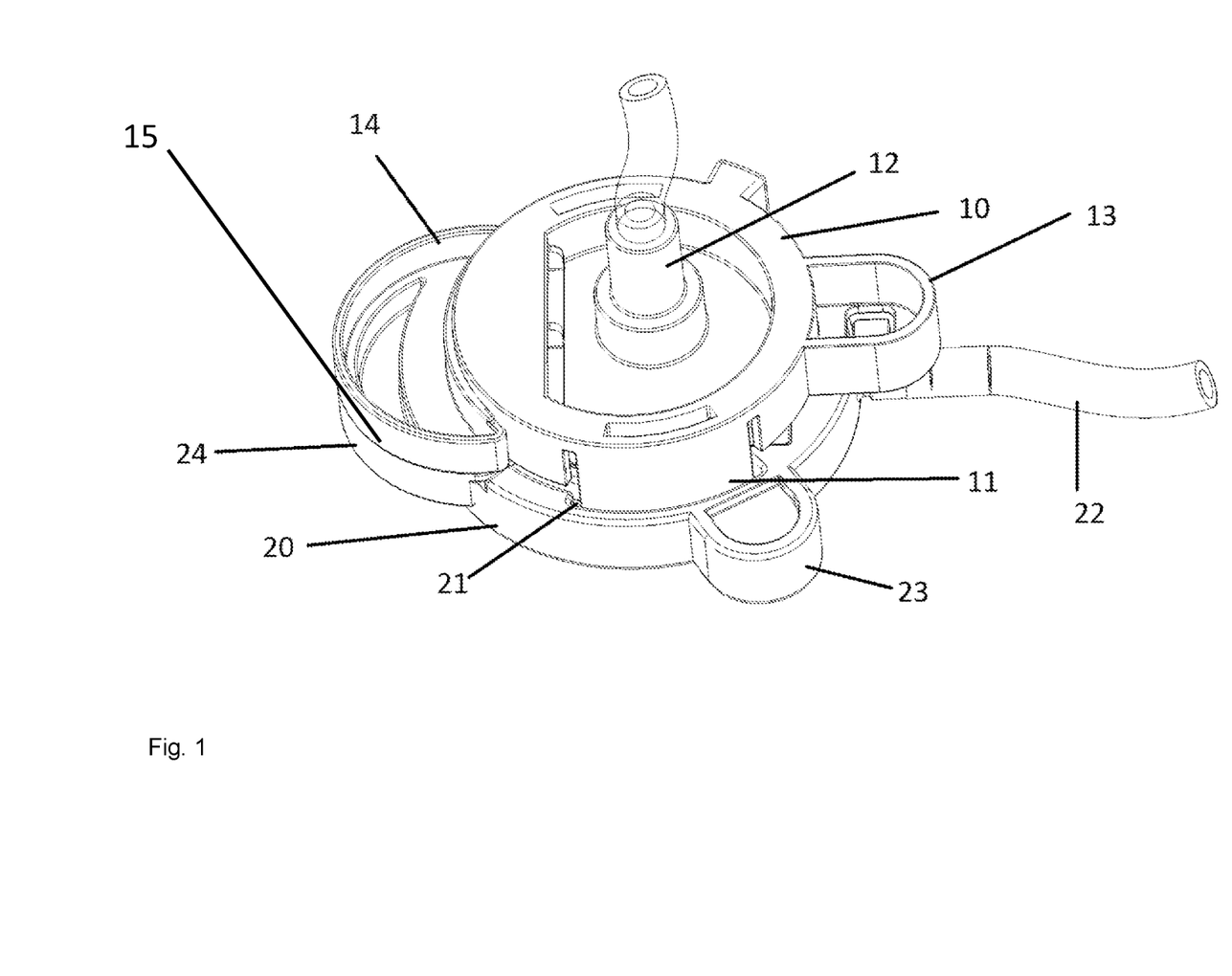
FIG. 1 shows an assembled connector of the invention with upper and lower part 10 and 20, complementary means for mechanically coupling 11 and 21, openings in the non-contact surfaces 12 and 22, means for mechanically interlocking 13 and 23, grips for releasable covering 14 and 24.
Figure 2:
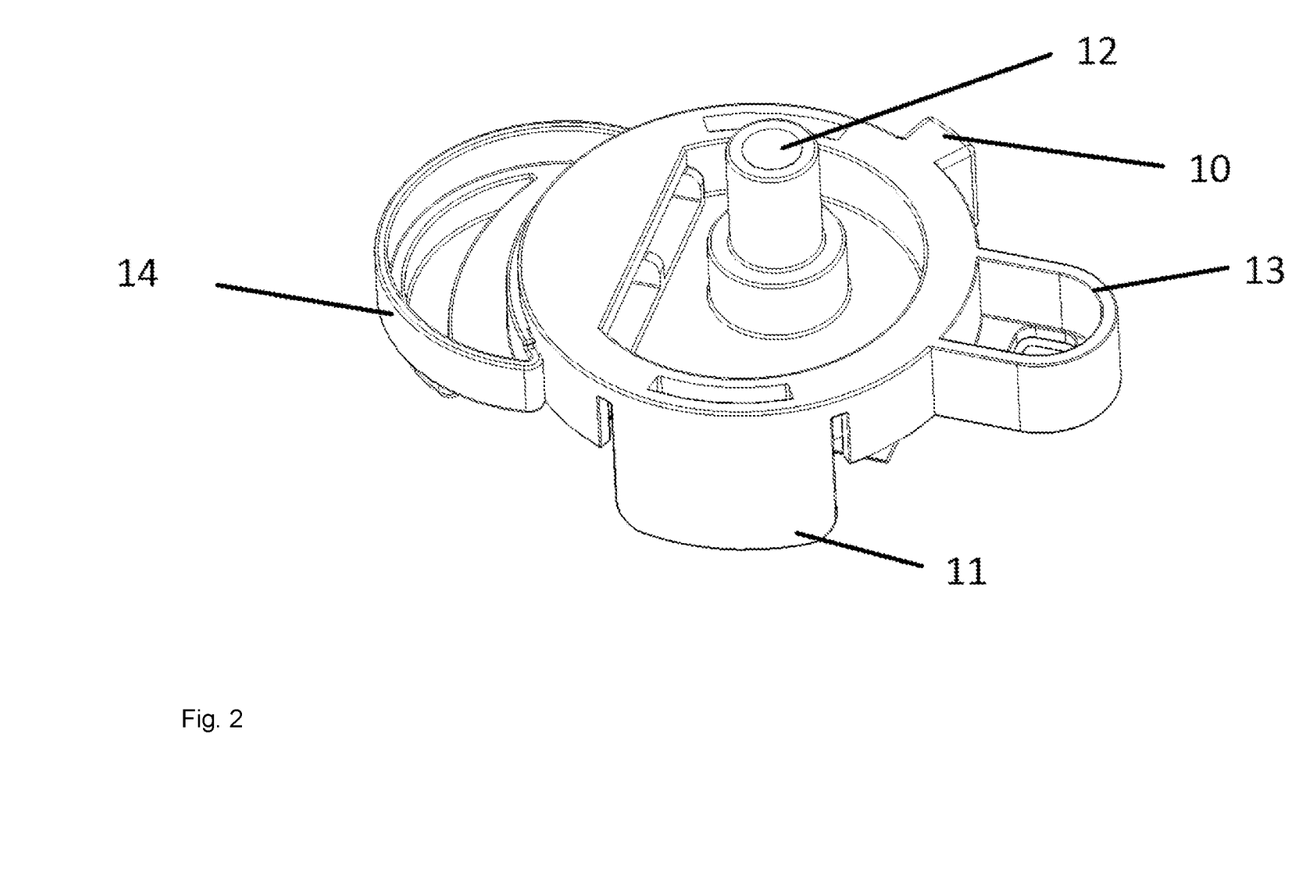
FIG. 2 shows one (upper) part (10) of the connector in top view with complementary means for mechanically coupling 11, opening in the non-contact surface 12, means for mechanically interlocking 13, grip for releasable covering 14.
Figure 3:
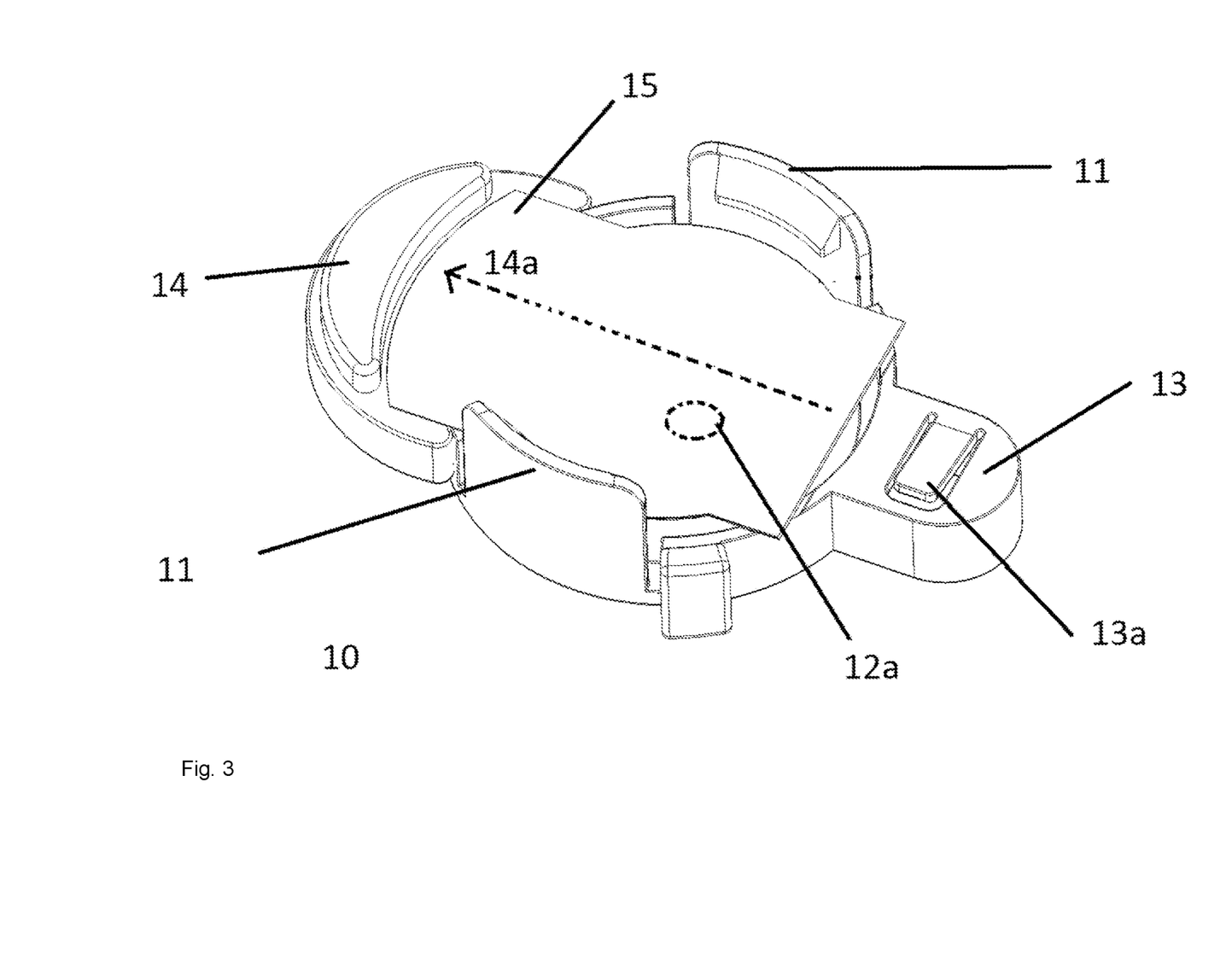
FIG. 3 shows one (upper) part (10) of the connector in bottom view with complementary means for mechanically coupling 11, opening in the contact surface 12a, means for mechanically interlocking 13, grip for releasable covering 14, releasable covering 15.
Figure 4:
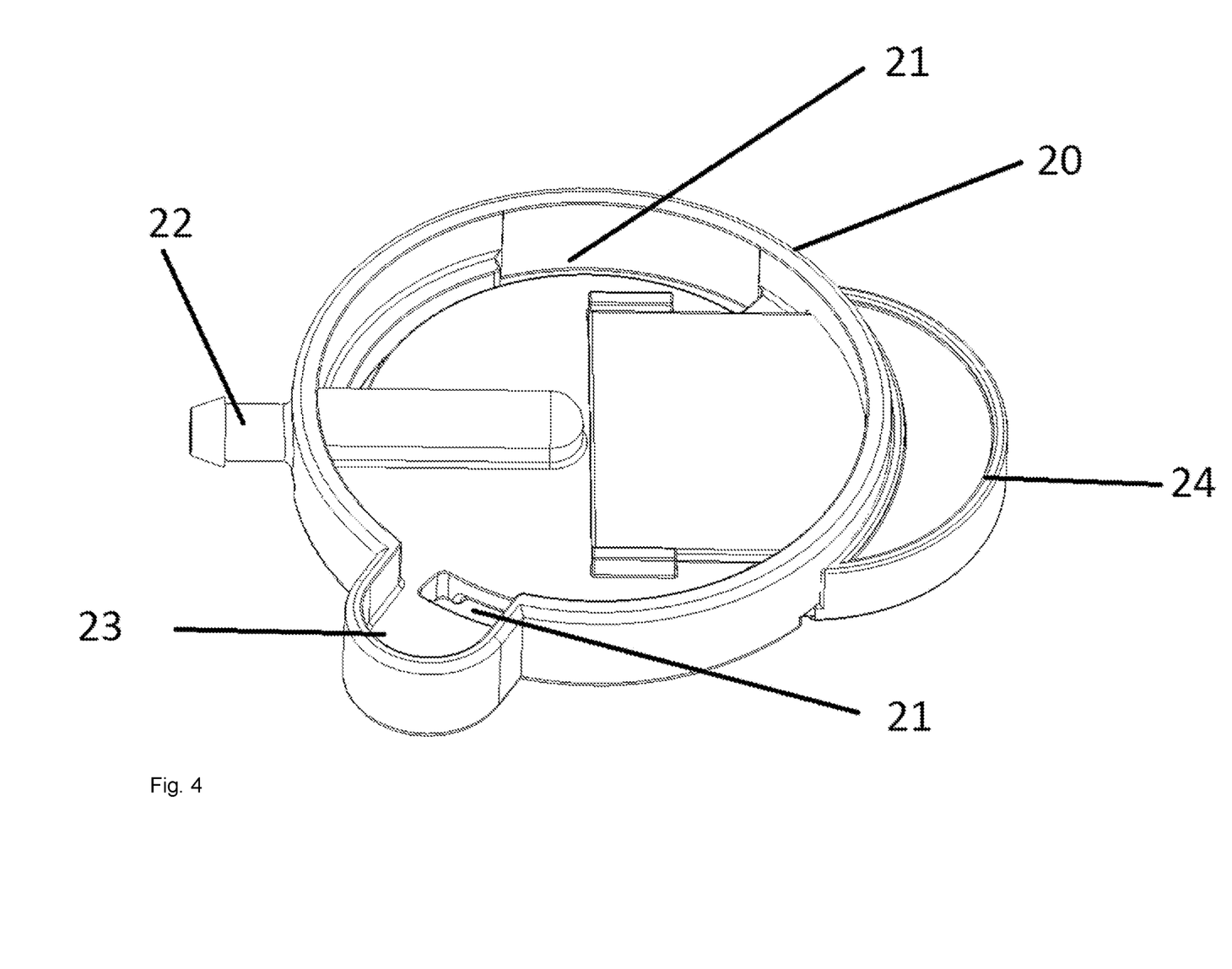
FIG. 4 shows one (lower) part (20) of the connector in top view complementary means for mechanically coupling 21, openings in the non-contact surface 22, means for mechanically interlocking 23, grip for releasable covering 24.
Figure 5:
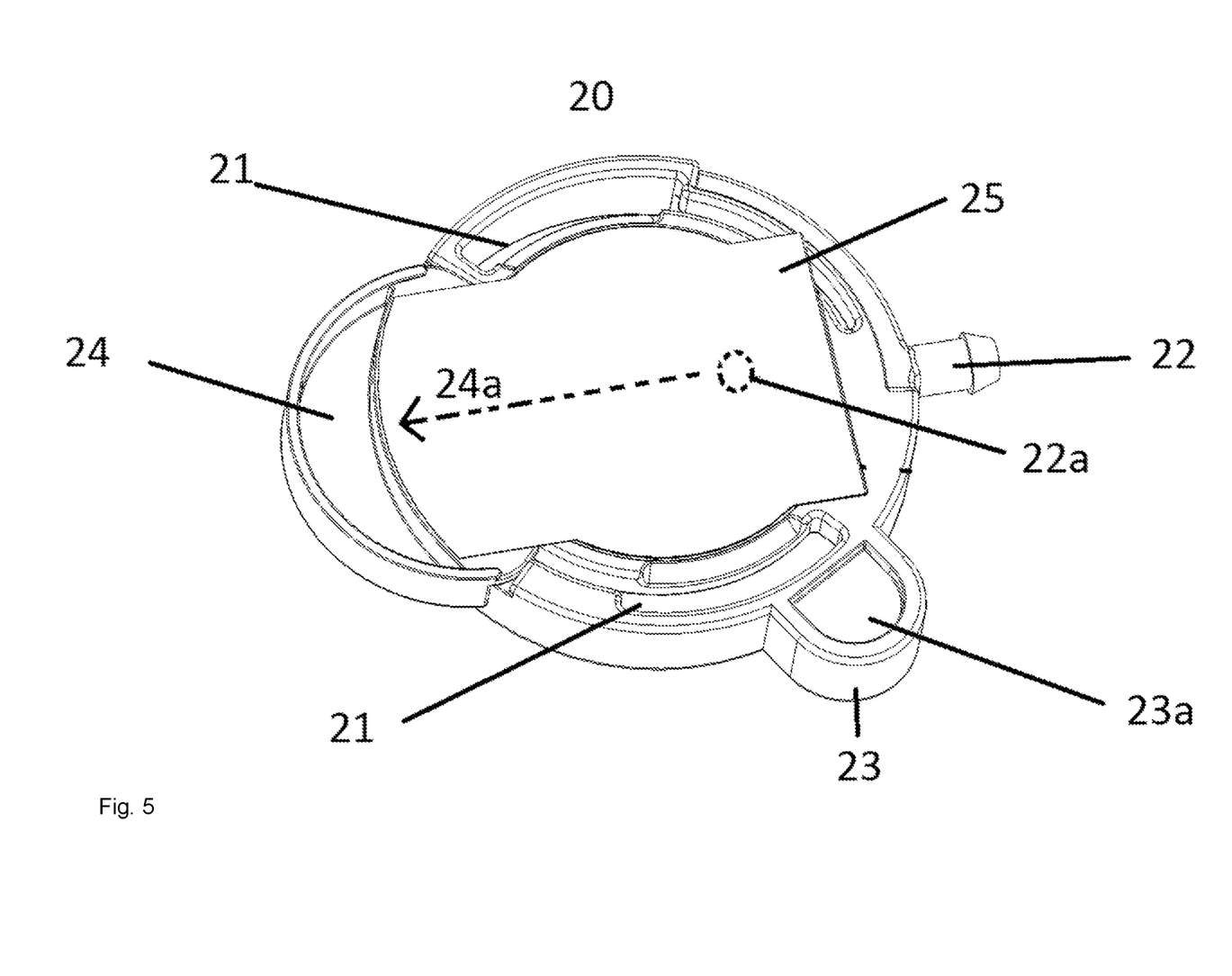
FIG. 5 shows one (lower) part (20) of the connector in bottom view with complementary means for mechanically coupling 21, openings in the contact surface 22a, means for mechanically interlocking 23, grip for releasable covering 24, releasable covering 25.
Figure 6:
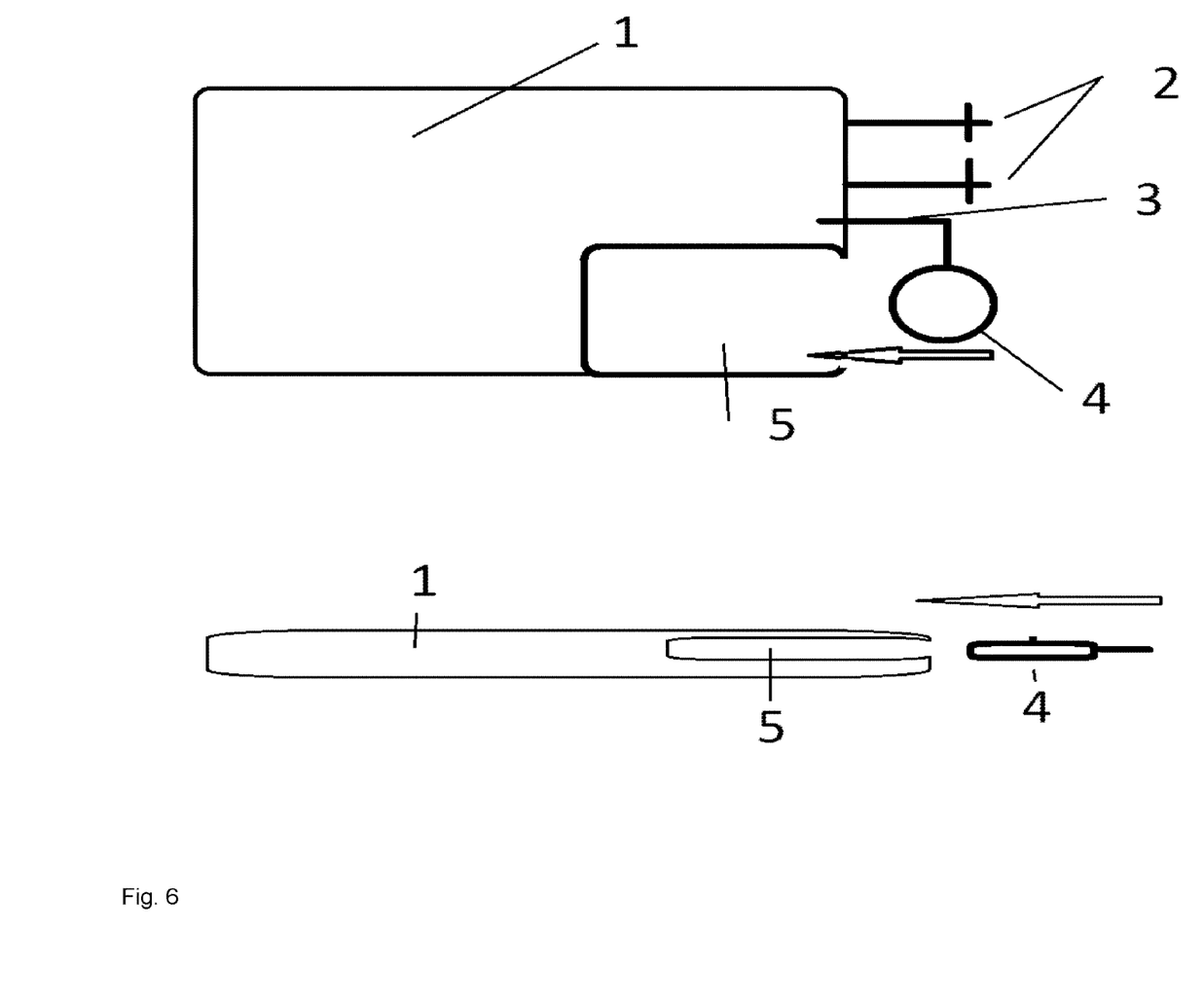
FIG. 6 shows the connector (4) with the freezing bag (1) having a recess (5) in top and side view. Usually freezing bags (1) have i/o ports for filling purposes (2). Tube (3) is in fluidic communication to sterile connector (4) which can be inserted into recess (5) for storage purposes.

In another embodiment, the openings of the first and second parts are located not in the rotational axis of first and second part which is defined by the centre of the counter-rotation of the first and second part during coupling. In other words, the openings in the contact surfaces of the first part and second part can only brought to match and provide fluid communication through the openings when the parts are rotated into the final, locked position. FIGS. 3 and 5 indicate the "asymmetric" position of the openings 12a and 22a.

Preferable, at least one of the openings of the first and second parts is provided with a gasket.

If the connector shall be fixed during operation at a stand or the like, it is preferred that the openings in the non-contact surfaces of at least one connector part are orthogonal to each other. In this variant (as shown in the drawings), one opening is located "on top" of one part and the other opening at a side of the other part of the connector. In other variants, both openings are located "on top" or at the side of both parts of the connector.

In order to connect the connector with tubes, the openings in the non-contact surfaces should be provided with an appropriate connecting adapter, especially with a Luer-lock adapter.

In another embodiment, the first part and second part are provided with means that prevent the openings in the contact surfaces of the first part and second part to be brought to match before the release coverings are removed from the openings and the parts are rotated to the locked position. This is shown in the figures, where the grips 14 and 24 are configured as recesses which interlock before both grips (and the release coverings) can be removed from the connector. Accordingly, grips 14 and 24 provide the means for preventing the releasable covering from being removed before the first and second ports are coupled. In some embodiments, the releasable coverings may be a sheet of flexible material with a fold. The flexible material may be removed by pulling out the fold as described below.

The connector according to the invention is provided with releasable coverings for the openings in the contact surfaces. The releasable coverings ensure that the openings and/or the contact surfaces are sterile up to the moment when the connector is used i.e. the releasable coverings are removed. The releasable coverings are preferable made from soft polymeric films like PE or PS or siliconized paper as known in the art and are glued or welded on the contact surfaces.

The connector/the parts of the connector is sterilized by processes known to a person skilled in the art, like autoclaving, irradiating or chemical treatment.

In a preferred variant of the invention, the releasable coverings of the openings in the contact surface are attached to extricable grips. "Attached" means that the releasable coverings are glued or mechanically bound to the extricable grips in a way that by extracting the grips from the parts of the connector, the releasable coverings are removed from the openings.

FIGS. 3 and 5 show the releasable coverings 15 and 25 attached to grips 14 and 24 in the respective parts of the connector. Grips 14 and 24 can be extracted from the parts in the direction as indicated by dotted lines 14a and 15a.

In order to prevent undesired loss of sterility by removing the releasable coverings subsequently and not simultaneously, the grips of the releasable coverings of the first part and second part are provided with complementary means for mechanically interlock with each other. This locking additional prevents an early counter-rotating of the first and second part.

Preferable, the first part and the second part is provided with means to prevent the release coverings from being removed from the openings before the first part and second part are mechanically coupled.

In a preferred embodiment, the releasable coverings are adhered as a folded double layer to the contact surfaces configured to be peeled off the openings by simultaneously removing the mechanically interlocked grips at least in part from the mechanically interlocked first part and second part.

The releasable coverings may be glued or welded to the contact surfaces.

In a further embodiment to ensure that sterility is maintained, the releasable coverings are simultaneously removed from the openings of the first part and second part by simultaneously removing the mechanically interlocked grips at least in part from the mechanically interlocked first part and second part.

In a further embodiment, the extricable grips are provided with a blocking means that prevents further counter-rotating of the first and second part until both grips are extracted from the interlocked parts. By extracting the grips, the blocking means is removed and further counter-rotating of the first and second part into the final position is possible. Optionally the openings of the parts are brought to match at least in part to provide fluid communication when the parts are rotated to the final position.

FIG. 7 illustrates another embodiment of the sterile connector, and shows a specimen holding structure. In this embodiment, an adhesive foil may be placed between the specimen-holding components. As shown in FIG. 7, the specimen holding structure may have an upper component 116 and a lower component 118. The upper component 116 may have a fluid coupling structure such as a hose barb, to which fluidic tubing may be coupled. The tubing may have an inner diameter of for example, about 6 mm and may be made of sterile, flexible, biocompatible material such a tygon or other polymer. IN other embodiments, the tubing may be made of polyurethane or silicone. The lower component 118 may also be provided with a fluidic coupling structure 119, which may accept another sterile, flexible, biocompatible tubing material. The fluidic coupling structures may be provided with contoured surfaces which reduce or eliminate leakage.

Accordingly, in one embodiment, the upper part 116 may be a "bag adapter" (which couples to e fluid storage bag) and the lower part 118 may be a "tubing set adapter" which couples to one or more tubes. More generally, however, both the upper 116 and the lower part 118 may define a two part connector that couples to fluid bags or fluidic tubing.

To create the fluidic structure, the upper component 116 may be connected to the lower component 118, to form a continuous fluid path. The coupled structure and the continuous fluid path are shown in FIG. 7B.

However, when coupling the upper component 116 to the lower component 118, the possibility exists of debris or other contamination landing on the exposed surfaces, which may allow contamination of the sample as the components are brought together. One object of this invention is to create a sterile connection between the upper, inlet component and the lower, output component.

To reduce the possibility of contamination being transferred between the upper component 116 and the lower component 118, a pair of thin, folded flexible sheets or foils 112 may be introduced to the components. The sheets may be provided at manufacture of the components, such that the surface against which the sheets are disposed are sterile, or these surfaces may first be sterilized before application of the sheets 112 to the surfaces. In any event, the sheets 112 may be provided with a fold 113, such that the sheets are continuous top to bottom. The adhesion of the foils or sheets may reduce possibility of contaminants on the foil contaminating the environment or user. This may reduce the risk from hazardous liquids inside the system. the encapsulation of the contamination to protect the environment and the user from the contamination. The special function of our sterile connector with adhesive foil is, that it is sterile (or at least protective) both ways: No contamination gets into the system, but also no hazardous material is easily or by accident accessible to the user.

The fold 113 may be used to withdraw the sheets or foils 112 from between the surfaces of the upper and lower components 116 and 118.

An adhesive film (heavy line shown in FIG. 7A) may be applied to the inner and/or outer surfaces of the sheets or fold. In particular, the adhesive material may be applied to the inner surfaces of the sheets or foils, such that the sheets or foils encapsulate any contamination present on the surfaces, as the sheets or foils are withdrawn. This feature is shown in FIG. 7C. The adhesive may also be applied to the outer surfaces, to promote adhesion to the upper and lower components 116 and 118, as well as to any contamination that may be present on these surfaces.

Accordingly, the addition of sheets or foils into the sterile connector may allow a last in-situ cleaning of the surfaces to improve cleanliness and maintain sterility of the components, immediately before joining the assembly together.

The sheets or foils may be metal or plastic for example. A biocompatible polymer material having sufficient flexibility may be used, or a metal sheet such as aluminum may be used. The adhesive may be any biocompatible material such as a silicone or polyester based adhesive. The thickness of the sheet or film or foil may be less than about at least about 0.01 mm thick and more preferably between about 0.05 and 0.15 mm thick. The lateral area may be whatever dimension needed to generally cover the surfaces, but on the order of several millimeters at least. The sheets or foils may be made by stamping from a roll of like material. The adhesive may be sprayed, rolled, painted or silk-screened on the flexible material, or the adhesive may be previously applied to the material, or may even be a characteristic of the material itself.

In one embodiment, the adhesive film may be only on one side of the tape, the side where contamination is possible or likely. Accordingly the foil or sheet may be dispensed on a roll with the adhesive on the inner surface of the roll. Because the sheet is folded, the "inner" versus "outer" surface may be better described as a "one side" and an "obverse side". But it should be understood that the foil or sheet may have adhesive on both sides, but in some embodiments, on just one side.

Figure 7A:
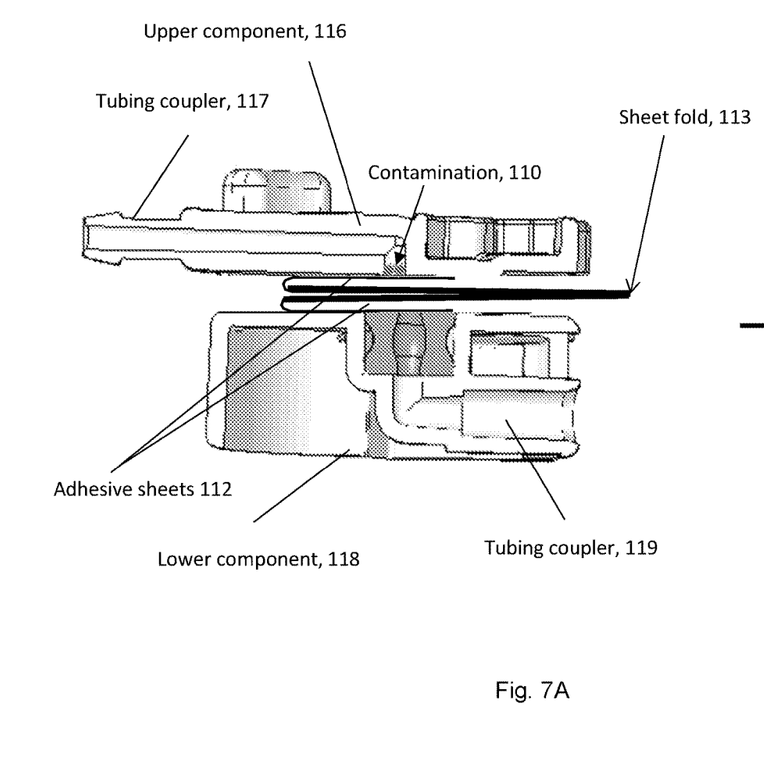
FIG. 7A shows the flexible sheet with adhesive disposed between the upper 116 and lower 118 parts.
Figure 7B:
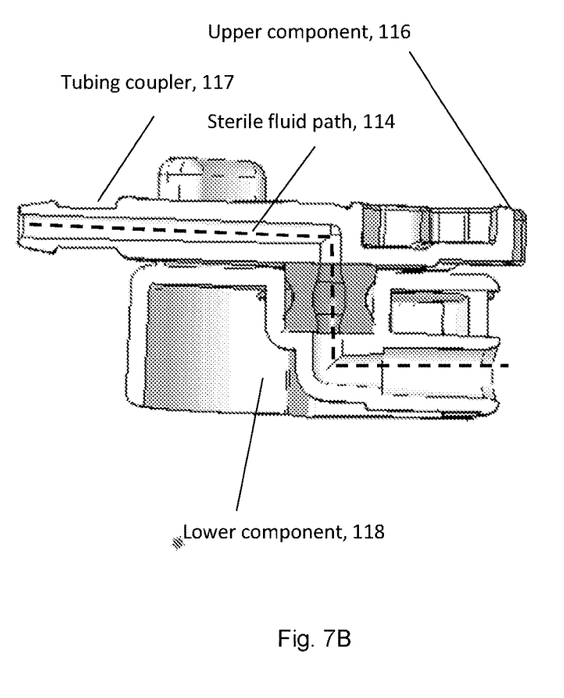
FIG. 7B shows the flexible sheet removed and the upper and lower parts joined.
Figure 7C:
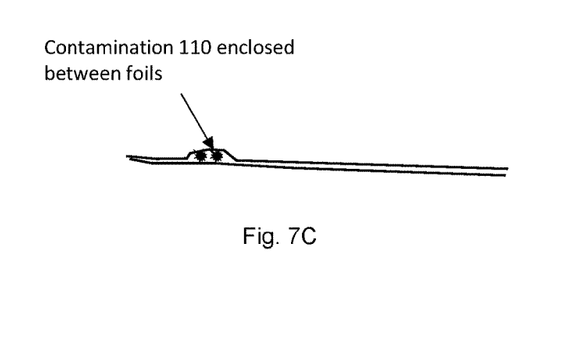
FIG. 7C shows the flexible sheet removed from the assembly and encapsulating contamination.

Accordingly, described here and illustrated in FIGS. 7A, 7B and 7C is a sterile connector comprising a first part and a second part. Each of the first part and the second part may be provided with a contact surface and at least one non-contact surface facing away from the contact surface, at least one opening in the contact surface having a fluid connection to at least one opening of the non-contact surface, a releasable covering of the opening in the contact surface. The sterile connector may further include a complementary means for mechanically coupling the parts at the contact surfaces to form the connector, and a sheet of flexible material with a fold, wherein the sheet of flexible material is adhered with a temporary adhesive to the first and second parts, and removed by pulling the fold away prior to mechanically coupling the first and the second parts.

The complementary means for mechanically coupling the parts are configured to mechanically interlock with each other by counter-rotating of the first and second part; and the openings in the contact surfaces are configured to be brought to match at least in part to provide fluid communication through the openings by counter-rotating of the first and second part. the sheet of flexible material may include a temporary adhesive on both the inner and the outer surfaces of the sheet of flexible material. The sheet of flexible material may have a thickness of at least about 0.01 mm thick and more preferably between about 0.05 and 0.15 mm thick., and comprises a biocompatible polymer. The connector according to claim 1, wherein the sheet of flexible material is removed by pulling the fold, such that the sheet of flexible material collapses together, encapsulating contamination between the surfaces of the sheet of flexible material.

It should be understood that this counter-rotation is one embodiment, but that the foils or sheets may be used with any two-part sterile connector.

Process of Manufacture of the Device

The device of the invention may be manufactured by any method known to a person skilled in the art. Preferred methods are injection molding and 3D printing, for example by extrusion deposition, fused deposition modeling, stereolithography or photopolymer digital light processing.

In a preferred variant, one part of the connector (like the first part) is fixed to the freezing bag and the respective other part (like the second part) is fixed to a tubing set.

The connector should be manufactured from materials certified for medical use and certified for stability at deep temperatures like −190° C. Examples for such materials are EVA and PE-UHMW or LCP (Ethylene Vinyl Acetat, Poly Ethylene Ultra High Molecular Weight, Liquid Crystal Polymere).

As mentioned previously, the sheet of flexible material may be stamped from a roll of like material having the desired thickness. The adhesive may be sprayed, rolled, painted or silk-screened on the flexible material, or the adhesive may be previously applied to the material, or may even be a characteristic of the material itself.

To assemble the connector, first the grip 14 or 24 are positioned with part 10 or 20 and the releasable covering 15 or 25, then the coverings are welded or glued onto the contact surfaces. The parts are now ready for sterilization.

Use of the Device

The device of the invention is configured to connect two tubes i.e. to provide fluid communication between two tubes in a sterile manner and therefore is provided with the above described safety means.

The handling sequence of the coupling process may further be described as follows:
1. Provide the two parts of the connector as described and place adjacent to each other with the respective contact surfaces. The flexible material may be folded between the contact surfaces, and removed by pulling the fold laterally, peeling the flexible sheet (along with any contamination thereon) laterally away from the two parts of the connector.
2. Slide-in the clips of the first into the matching gaps of the second part, thereby mechanically interlocking the parts and additional interlocking the extricable grips.
3. Simultaneously remove the interlocked grips at least in part from the mechanically interlocked first part and second part and simultaneously removing the a releasable covering of the openings and removing the blocking means
4. Further counter-rotate the first and second part into the final position thereby bringing the openings of the parts to match at least in part to provide fluid communication between the openings and connected tubing set.

While various details have been described in conjunction with the exemplary implementations outlined above, various alternatives, modifications, variations, improvements, and/or substantial equivalents, whether known or that are or may be presently unforeseen, may become apparent upon reviewing the foregoing disclosure. For example, while the disclosure describes a number of fabrication steps and exemplary dimensions for the device, it should be understood that these details are exemplary only, and that the systems and methods disclosed here may be applied to any number of alternative designs. Accordingly, the exemplary implementations set forth above, are intended to be illustrative, not limiting.

What is claimed is:

1. A medical device comprising: a first part and a second part, each provided with:
   a contact surface and at least one non-contact surface facing away from the contact surface;
   at least one opening in the contact surface having a fluid connection to at least one opening of the non-contact surface;
   a releasable covering comprising a sheet of flexible material which is adhered to the contact surface by a fold in the sheet of flexible material, wherein the sheet of flexible material covers the opening in the contact surface;
   complementary means for mechanically coupling the parts at the contact surfaces to form the connector; and
   wherein the sheet of flexible material is adhered to the contact surface with a temporary adhesive, and removed by pulling the fold away prior to mechanically coupling the first and the second parts, and characterized in that the openings of the first and second parts are not located in a rotational axis defined by a centre of counter-rotation of the first and second parts during coupling; and
   a medical tubing set, comprising at least one freeze bag coupled to the connector and at least one tube, wherein the at least one freeze bag comprises at least one recess into which the connector is inserted, with the freeze bag and connector in fluid communication within the recess, to accommodate at least one connector.

2. The medical device according to claim 1 wherein, the complementary means for mechanically coupling the parts are configured to mechanically interlock with each other by counter-rotation of the first and second parts; and the openings in the contact surfaces are configured to be brought to match at least in part to provide fluid communication through the openings by counter-rotation of the first and second parts.

3. The medical device according to claim 1, wherein the sheet of flexible material includes the temporary adhesive on both the inner and the outer surfaces of the sheet of flexible material.

4. The medical device according to claim 1, wherein the releasable coverings of the openings in the contact surfaces are attached to extricable grips, wherein the extricable grips are the grips of the releasable coverings of the first part and second part and are provided with complementary means for mechanically interlocking with each other.

5. The medical device according to claim 1, wherein the sheet of flexible material has a thickness of at least 0.01 mm, and comprises a biocompatible polymer.

6. The medical device according to claim 1, wherein the sheet of flexible material is removed by pulling the fold, such that the sheet of flexible material collapses together, encapsulating contamination between the surfaces of the sheet of flexible material.

7. The medical device according to claim 1, wherein the temporary adhesive is at least one of a biocompatible silicone adhesive or a polyester adhesive.

8. The medical device according to claim 1, characterized in that the first and second parts are provided with means to optically indicate the relative position of the first and second parts to each other during counter-rotation of the parts.

9. The medical device according to claim 1, characterized in that at least one of the openings of the first and second parts is provided with a gasket.

10. The medical device according to claim 1, characterized in that the openings in the non-contact surfaces of the first and the second parts are orthogonal to each other.

11. The medical device according to claim 1, characterized in that the openings in the non-contact surfaces are provided with a Luer-lock adapter.

* * * * *